United States Patent
Zhang et al.

(10) Patent No.: US 9,302,979 B2
(45) Date of Patent: Apr. 5, 2016

(54) METHOD FOR PREPARATION OF BIS (2-DIALKYLAMINOETHYL) ETHER

(71) Applicant: SICHUAN ZHIJIANG ADVANCED MATERIALS CO., LTD., Suining, Sichuan (CN)

(72) Inventors: Chao Zhang, Sichuan (CN); Hua Zhang, Sichuan (CN); Xiaoming Ye, Sichuan (CN); Qi Zhang, Sichuan (CN); Chuanwei Ye, Sichuan (CN)

(73) Assignee: SICHUAN ZHIJIANG ADVANCED MATERIALS CO., LTD., Suining, Sichuan Province (CN)

( * ) Notice: Subject to any disclaimer, the term of this patent is extended or adjusted under 35 U.S.C. 154(b) by 0 days.

(21) Appl. No.: 14/681,054

(22) Filed: Apr. 7, 2015

(65) Prior Publication Data

US 2015/0291506 A1     Oct. 15, 2015

(30) Foreign Application Priority Data

Apr. 9, 2014  (CN) .......................... 2014 1 0139567

(51) Int. Cl.
    *C07C 213/10*     (2006.01)
    *C07C 213/06*     (2006.01)
(52) U.S. Cl.
    CPC ............. *C07C 213/10* (2013.01); *C07C 213/06* (2013.01)

(58) Field of Classification Search
    None
    See application file for complete search history.

(56) References Cited

U.S. PATENT DOCUMENTS 3,480,675 A * 11/1969 Poppelsdorf ........... C08G 18/18
                                                     502/167

OTHER PUBLICATIONS

Database CAPLUS in STN, Acc. No. 2011:1664501, Shi, CN 102285892 A (Dec. 21, 2011) (abstract).*
Database CAPLUS in STN, Acc. No. 2009:354965, Wang et al., Huaxue Shijie (2009), 50(2), pp. 97-99, 103 (abstract).*

* cited by examiner

*Primary Examiner* — Brian J Davis

(57) ABSTRACT

A bis (2-dialkylaminoethyl) ether synthesizing method is disclosed, which includes steps of: 1) synthesizing: wherein N,N-dialkylethanolamine, N,N-dialkylamine and ethyne are mixed at a mole ratio of 4:3:1-2:1:1 as a raw material; and the raw material, catalyst and solvent are added in a high-pressure clave for reaction in a sealed condition; a weight of catalyst accounts for 2.0%-10.5% of the total weight of the raw material; a reaction temperature is 50-120° C. and the reaction time is 3-7 hours; the clave is then opened after reaction and a filtrate is collected by filtering the reaction mixture; and 2) separating: wherein the filtrate obtained in the step 1) is rectified to obtain the bis (2-dialkylaminoethyl) ether as a product. The synthetic method of the bis (2-dialkylaminoethyl) ether in the present invention has many characteristics, such as simple process, high atomic economy, etc.

10 Claims, No Drawings

METHOD FOR PREPARATION OF BIS (2-DIALKYLAMINOETHYL) ETHER

CROSS REFERENCE OF RELATED APPLICATION

The present invention claims priority under 35 U.S.C. 119 (a-d) to CN 201410139567.7, filed Apr. 9, 2014.

BACKGROUND OF THE PRESENT INVENTION

1. Field of Invention

The present invention relates to a new method for preparation of bis (2-dialkylaminoethyl) ether.

2. Description of Related Arts

Bis (2-dialkylaminoethyl) ether, is an important kind of organic chemical intermediate, which can be used as a catalyst for polyurethane foam synthesis. And the general chemical structure of it was shown in S-1.

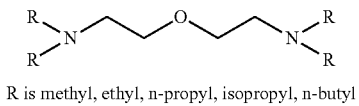

R is methyl, ethyl, n-propyl, isopropyl, n-butyl

According to -the related literatures, bis (2-dialkylaminoethyl) ether is prepared mainly by the following method currently:

1) Etherification reaction between N,N-dialkylchloroethylamine and N,N-dialkylethanolamine sodium salt is employed to obtain the target compound. The reaction temperature is above 100° C. and the reaction time is 6 hours, the product yield is around 60%. In this method, a lot of chloride sodium is produced as side product and the reaction environment is strongly corrosive.

2) The above method has been improved in literatures by using N,N-dialkylethanolamine sodium and N,N-dialkylethanolamine as the raw materials and chlorosulfonic acid, sulfoxide chloride and sulfonyl chloride were added as chloridizing agents in one pot. Long-chain alkane was used as solvent, and the reaction temperature is 50-100° C. The yield rate is around 50% after reacting about 3 hours. However, the defects of the original method still remain.

3) In patent U.S. Pat. No. 4,247,482 (1981), a method was reported by using N,N-dialkylethanolamine sodium salt as raw material and sulfur trioxide as catalyst. The reaction temperature is 110° C. and the reaction time is over 5 hours; the yield rate is around 61%. The main shortcoming of that method is that the way to feed sulfur trioxide is trivial and sulfur trioxide is not environmentally friendly.

4) In patent U.S. Pat. No. 4,474,988 (1984), a continuous reaction was reported by using N,N-dialkylethanolamine as raw material and solid alkaline zeolite as catalyst. The reaction temperature is 325° C. and the reaction time is 5 hours. The N,N-dialkylethanolamine conversion rate reaches over 90%. However, the selectivity of the target product is lower than 20%. The shortcomings of this method are high reaction temperature, poor selectiveness and low yield rate.

Therefore, there are still some defects in the currently available methods for preparation of bis (2-dialkylaminoethyl) ether, which are urgent to solve and improve.

SUMMARY OF THE PRESENT INVENTION

The technical problem to be solved by the present invention is to provide a simple bis (2-dialkylaminoethyl) ether synthesizing method with high atomic economy.

To solve the above technical problems, the present invention provides a new bis (2-dialkylaminoethyl) ether synthesizing method, which includes the following steps:

1) synthesizing:
wherein N,N-dialkylethanolamine, N,N-dialkylamine and ethyne are mixed at a mole ratio of 4:3:1-2:1:1 as a raw material; the raw material, catalyst and solvent are added in a high-pressure clave for reaction in a sealed condition; a weight of catalyst is about 2.0%-10.5% of the total weight of the raw material; a reaction temperature is 50-120° C. and the reaction time is 3-7 hours; after reaction, the catalyst is removed by filtering and a filtrate is collected; and 2) separating:
wherein the filtrate obtained in the step 1) is then rectified with the bis (2-dialkylaminoethyl) ether as product.

As an improvement to the bis (2-dialkylaminoethyl) ether synthesizing method in the present invention:
in the step 2):
solvent and excessive, the N,N-dialkylethanolamine and the N,N-dialkylamine are collected as the raw materials.

Remarks: In the present invention, most of ethyne is consumed in the reaction. The remaining ethyne is too little to collect due to a low boiling point thereof. Therefore, ethyne collection is not considered in the present invention.

As a further improvement to the synthetic method for bis (2-dialkylaminoethyl) ether in the present invention:

when the N,N-dialkylethanolamine is N,N-dimethylethanolamine and the N,N-dialkylamine is dimethylamine, the product obtained is bis (2-dimethylaminoethyl) ether;

when the N,N-dialkylethanolamine is N,N-diethylethanolamine and the N,N-dialkylamine is diethylamine, the product obtained is bis (2-diethylaminoethyl) ether;

when the N,N-dialkylethanolamine is N,N-dinpropylethanolamine and the N,N-dialkylamine is dinpropylamine, the product obtained is bis (2-dinpropylaminoethyl) ether;

when the N,N-dialkylethanolamine is N,N-diisoethylethanolamine and the N,N-dialkylamine is diisoethylamine, the product obtained is bis (2-diisopropylaminoethyl) ether;

when the N,N-dialkylethanolamine is N,N-dinbutylethanolamine and the N,N-dialkylamine is dinbutylamine, the product obtained is bis (2-dinbutylaminoethyl) ether.

As a further improvement to the synthetic method of bis (2-dialkylaminoethyl) ether in the present invention: the catalyst includes potassium hydroxide, sodium hydroxide, sodium ethoxide and potassium ethoxide.

As a further improvement to the synthetic method of bis (2-dialkylaminoethyl) ether in the present invention, the solvents include dinbutyl ether, diisobutyl ether, 1,3-dioxolane, 1,3-dioxane and 1,4-dioxane.

As a further improvement to the synthetic method of bis (2-dialkylaminoethyl) ether in the present invention, a mass ratio between the solvents and raw materials is 1-2:1.

In the present invention, a room temperature is 15-25° C. without exception.

A reaction formula of bis (2-dialkylaminoethyl) ether in the present invention is shown in the following formula S-2:

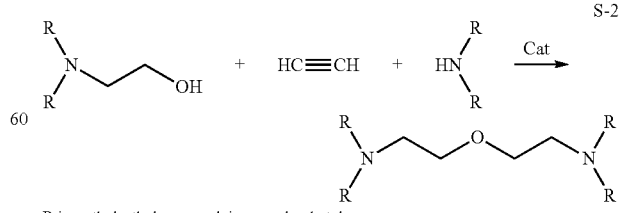

R is methyl, ethyl, n-propyl, isopropyl, n-butyl

The synthetic method of bis (2-dialkylaminoethyl) ether in the present invention has the following advantages:

1) One-pot reaction makes it easy to operate and shortens the reaction flow;

2) It has a high atomic economy because the reaction process does not contain any intermediate containing halogen atom and the utilization ratio of raw materials is high, and hence the costs and emission is reduced;

3) It has a wide supply of the raw material, and the reaction condition is mild (the reaction temperature is low and the reaction environment is not corrosive). The equipment operation requirement is low and the post treatment is simple. Hence, the present invention is suitable for industrialization as a result of reducing the burden of three-waste treatment substantially and the harm to environment and human beings.

These and other objectives, features, and advantages of the present invention will become apparent from the following detailed description, and the appended claims.

DETAILED DESCRIPTION OF THE PREFERRED EMBODIMENT

Preparation of Bis (2-Dimethylaminoethyl) Ether

Example 1 a bis (2-dimethylaminoethyl) ether synthesizing method using N,N-dimethylethanolamine, dimethylamine and ethyne as raw materials (original raw materials) is performed by the following operations in proper order:

step 1: synthesizing:

wherein at a room temperature, 89 g N,N-dimethylethanolamine (1.0 mol), 124.5 g dinbutyl ether (as a solvent) and 8.7 g potassium hydroxide are added in a high-pressure reaction clave with a mixing and temperature-measuring device; and the clave cover is put on and leakage is inspected, then 13 g ethyne (0.5 mol) and 22.5 g dimethylamine (0.5 mol) are forced into the clave in proper order; after feeding, a temperature is raised to 100° C. and kept on for 5 h before the reaction ends;

after reaction, the clave is opened and a filtrate is obtained by filtering the reaction mixtures; and step 2: separating:

wherein the filtrate obtained is then distilled at 40° C. and atmospheric pressure for half an hour and unreacted dimethylamine will come out; after doing that, rectification at reduced pressure intermittently is proceeded; at a pressure of 1 kPa, the previous fractions (all fractions before 69° C.) —unreacted N,N-dimethylethanolamine and solvent are collected; the fractions at 69-72° C. are collected and bis (2-dimethylaminoethyl) ether obtained weighs 72.3 g; a product purity is 98.5%; and a yield is 90.4%, by taking the consumed ethyne as the reference.

The dimethylamine distilled out at atmospheric pressure can be collected with the previous fractions for next reaction.

Preparation of Bis (2-Diethylaminoethyl) Ether

Example 2 a bis (2-diethylaminoethyl) ether synthesizing method using N,N-diethylethanolamine, diethylamine and ethyne as raw materials (original raw materials) is performed by the following steps in proper order:

step 1: synthesizing:

wherein at a room temperature, 117 g N,N-diethylethanolamine (1.0 mol), 268 g diisobutyl ether (as a solvent) and 3.6 g sodium ethoxide are added in a high-pressure reaction clave with a mixing and temperature-measuring device; the clave cover is put on and leakage is inspected; then 6.5 g ethyne (0.25 mol) and 55.0 g diethylamine (0.75 mol) are forced into the clave in proper order; after feeding, a temperature is raised to 50° C., and kept on for 7 h before completing the reaction;

after reaction, the clave is opened and a filtrate is obtained by filtering the reaction mixture; and step 2:

distilling the filtrate obtained at 60° C. and atmospheric pressure for half an hour for the unreacted diethylamine to come out; then proceeding to rectification at reduced pressure intermittently; at a pressure of 1 kPa, collecting the previous fractions (all fractions before 91° C.)—unreacted N,N-diethylethanolamine and solvent; then collecting the fractions at 91-93° C. and obtaining bis (2-diethylaminoethyl) ether weighing 51.5 g; wherein a product purity is 99.1%; by taking the consumed ethyne as reference, a yield rate is 95.3%.

Preparation of Bis (2-Dinpropyaminoehyl) Ether

Example 3 a bis (2-dinpropylaminoethyl) ether synthetic method using N,N-dinpropylethanolamine, dinpropylamine and ethyne raw materials (original raw materials) to perform the following steps in proper order:

step 1:

at a room temperature, adding 145 g N,N-dinpropylethanolamine (1.0 mol), 508 g 1,3-dioxolane (as solvent) and 25.4 g sodium hydroxide in a high-pressure reaction clave with a mixing and temperature-measuring device; putting the clave cover on and inspect leakage; forcing in 8.7 g ethyne (0.33 mol) and 101 g dinpropylamine (1.0 mol) in a proper order; after feeding, raising a temperature to 120° C.; holding the above reaction temperature and reacting for 3 h before completing the reaction;

opening the clave after reaction and filter; collecting a filtrate obtained; and step 2:

for the filtrate obtained at a pressure of 1 kPa, collecting previous fractions (all fractions before 180° C.)—unreacted dinpropylamine, N,N-dinpropylethanolamine and solvent; then collecting the fractions at 180-183° C. and obtaining bis (2-dinpropylaminoethyl) ether weighing 83.6 g; wherein a product purity is 97.6%; by taking the consumed ethyne as reference, a yield rate is 93.1%.

Preparation of Bis (2-Diisopropylaminoehyl) Ether

Example 4 a bis (2-diisopropylaminoethyl) ether synthesizing method using N,N-diisoethylethanolamine, diisoethylamine and ethyne as raw materials (original raw materials) to perform the following steps in proper order:

step 1:

at a room temperature, adding 145 g N,N-diisoethylethanolamine (1.0 mol), 382 g 1,3-dioxane (as solvent) and 12.7 g potassium hydroxide in a high-pressure reaction clave with a mixing and temperature-measuring device; putting the clave cover on and then press in 8.7 g ethyne (0.33 mol) and 101 g diisoethylamine (1.0 mol) in a proper order; after feeding, raising a temperature to 120° C.; holding the above temperature and reacting for 3 h before completing the reaction;

opening the clave after reaction and filter; collecting a filtrate obtained.

step 2:

rectifying the filtrate obtained at reduced pressure intermittently; at a pressure of 1 kPa, collecting the previous fractions (all fractions before 158° C.)—unreacted diisoethylamine, N,N-diisoethylethanolamine and solvent; then collecting the fractions at 158-161° C. and obtaining bis (2-diisopropylaminoethyl) ether weighing 76.8 g; wherein a product purity is 98.6%; by taking the consumed ethyne as reference, a yield rate is 85.6%.

Preparation of Bis (2-Dinbutyaminoehyl) Ether

Example 5 a kind of bis (2-dinbutylaminoethyl) ether synthesizing method using N,N-dinbutylethanolamine, dinbutylamine and ethyne as original raw materials to perform the following steps in proper order:

step 1:

at a room temperature, adding 173 g N,N-dinbutylethanolamine (1.0 mol), 261 g 1,4-dioxane (as solvent) and 21 g potassium ethoxide in a high-pressure reaction clave with a mixing and temperature-measuring device; putting the clave cover on and inspect leakage; then forcing in 10.4 g ethyne (0.4 mol) and 77.4 g dinbutylamine (0.6 mol) in a proper order; after feeding, raising a temperature to 100° C.; holding the above temperature and reacting for 4 h before completing the reaction;

opening the clave after reaction and filter; collecting afiltrate obtained; and step 2:

rectifying the filtrate obtained at reduced pressure intermittently; at a pressure of 1 kPa, collecting the previous fractions (all fractions before 222° C.)—unreacted dinbutylamine, N,N-dinbutylethanolamine and solvent; then collecting the fractions at 222-224° C. and obtaining bis (2-dinbutylaminoethyl) ether weighing 125.4 g; wherein a product purity is 98.1%; by taking the consumed ethyne as reference, a yield rate is 95.6%.

Results and Discussions

For proportion 1, the method, in relation to example 2, is only subject to the following modification that 3.6 g sodium ethoxide is changed into 3.6 g potassium hydroxide and the rest is the same as example 2.

Bis (2-diethylaminoethyl) ether obtained is 48.5 g. The product purity is 98.9%; by taking the consumed ethyne as reference, the yield is 89.7%.

For proportion 2, the method, in relation to example 2, is only subject to the following medication that 3.6 g sodium ethoxide is changed into 3.6 g sodium hydroxide and the rest is the same as example 2.

Bis (2-diethylaminoethyl) ether obtained is 46.5 g. The product purity is 99.1%; by taking the consumed ethyne as the reference, the yield is 86.0%.

For proportion 3, the method, in relation to example 2, is only subject to the following modification that 3.6 g sodium ethoxide is changed into 3.6 g potassium ethoxide; the rest is the same as example 2.

Bis (2-diethylaminoethyl) ether obtained is 50.5 g. The product purity is 99.2%; by taking the consumed ethyne as reference, the yield is 93.4%.

Finally, what should be noted is that the above embodiments are only some specific embodiments of the present invention. Obviously, the present invention is not limited to the above embodiments and there are a lot of variations. All variations from the contents of the present invention, which could be derived directly and thought out by the ordinary technical people, should be deemed as falling in the range of protection for the present invention without exception.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A bis (2-dialkylaminoethyl) ether synthesizing method comprising steps of:
   i) synthesizing:
      wherein N,N-dialkylethanolamine, N,N-dialkylamine and ethyne are mixed at a mole ratio of 4:3:1 or 2:1:1 as a raw material;
      the raw material, catalyst and solvent are added in a high-pressure autoclave for reaction in a sealed condition; a weight of catalyst accounts for 2.0%-10.5% of the total weight of the raw material; a reaction temperature is 50-120° C. and the reaction time is 3-7 hours; and the autoclave is opened after reaction, the catalyst is removed by filtering and a filtrate is collected; and
   ii) separating:
      wherein the filtrate obtained in the step i) is rectified with bis (2-dialkylaminoethyl) ether as product.

2. The bis (2-dialkylaminoethyl) ether synthesizing method, as recited in claim 1, wherein
   in the step ii):
   solvent and excessive, the N,N-dialkylethanolamine and the N,N-dialkylamine, are collected as the raw material.

3. The bis (2-dialkylaminoethyl) ether synthesizing method, as recited in claim 1, wherein:
   when the N,N-dialkylethanolamine is N,N-dimethylethanolamine and the N,N-dialkylamine is dimethylamine, the product obtained is bis (2-dimethylaminoethyl) ether;
   when the N,N-dialkylethanolamine is N,N-diethylethanolamine and the N,N-dialkylamine is diethylamine, the product obtained is bis (2-diethylaminoethyl) ether;
   when the N,N-dialkylethanolamine is N,N-dinpropylethanolamine and the N,N-dialkylamine is dinpropylamine, the product obtained is bis (2-dinpropylaminoethyl) ether;
   when the N,N-dialkylethanolamine is N,N-diisopropylethanolamine and the N,N-dialkylamine is diisopropylamine, the product obtained is bis (2-diisopropylaminoethyl) ether;
   when the N,N-dialkylethanolamine is N,N-dinbutylethanolamine and the N,N-dialkylamine is dinbutylamine, the product obtained is bis (2-dinbutylaminoethyl) ether.

4. The bis (2-dialkylaminoethyl) ether synthesizing method, as recited in claim 2, wherein:
   when the N,N-dialkylethanolamine is N,N-dimethylethanolamine and the N,N-dialkylamine is dimethylamine, the product obtained is bis (2-dimethylaminoethyl) ether;

when the N,N-dialkylethanolamine is N,N-diethylethanolamine and the N,N-dialkylamine is diethylamine, the product obtained is bis (2-diethylaminoethyl) ether;

when the N,N-dialkylethanolamine is N,N-dinpropylethanolamine and the N,N-dialkylamine is dinpropylamine, the product obtained is bis (2-dinpropylaminoethyl) ether;

when the N,N-dialkylethanolamine is N,N-diisopropylethanolamine and the N,N-dialkylamine is diisopropylamine, the product obtained is bis (2-diisopropylaminoethyl) ether;

when the N,N-dialkylethanolamine is N,N-dinbutylethanolamine and the N,N-dialkylamine is dinbutylamine, the product obtained is bis (2-dinbutylaminoethyl) ether.

5. The bis (2-dialkylaminoethyl) ether synthesizing method, as recited in claim 3, wherein the catalyst is potassium hydroxide, sodium hydroxide, sodium ethoxide or potassium ethoxide.

6. The bis (2-dialkylaminoethyl) ether synthesizing method, as recited in claim 4, wherein the catalyst is potassium hydroxide, sodium hydroxide, sodium ethoxide or potassium ethoxide.

7. The bis (2-dialkylaminoethyl) ether synthesizing method, as recited in claim 5, wherein the solvent is dinbutyl ether, diisobutyl ether, 1,3-dioxolane, 1,3-dioxane or 1,4-dioxane.

8. The bis (2-dialkylaminoethyl) ether synthesizing method, as recited in claim 6, wherein the solvent is dinbutyl ether, diisobutyl ether, 1,3-dioxolane, 1,3-dioxane or 1,4-dioxane.

9. The bis (2-dialkylaminoethyl) ether synthesizing method, as recited in claim 7, wherein a mass ratio between the solvent and the raw material is 1-2:1.

10. The bis (2-dialkylaminoethyl) ether synthesizing method, as recited in claim 8, wherein a mass ratio between the solvent and the raw material is 1-2:1.

\* \* \* \* \*